US006537535B1

(12) United States Patent
Williams

(10) Patent No.: US 6,537,535 B1
(45) Date of Patent: *Mar. 25, 2003

(54) TOTAL SCENT CONTROL SYSTEM

(76) Inventor: James Ronald Williams, 322 Old Plantation Rd., Jekyll Island, GA (US) 31527

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/004,848

(22) Filed: Jan. 9, 1998

(51) Int. Cl.[7] ................................................. A61L 9/00
(52) U.S. Cl. .................... 424/76.1; 424/76.2; 424/76.5; 424/400; 424/401
(58) Field of Search ............................. 424/76.1, 76.2, 424/76.5, 400, 401

(56) References Cited

U.S. PATENT DOCUMENTS

| 109,495 A | 11/1870 | Marshall |
| 214,375 A | 4/1879 | Knab ........................ D23/149 |
| 346,437 A | 7/1886 | Poblete ..................... D23/371 |
| 3,516,232 A | * 6/1970 | Gilbertson .................... 55/385 |
| 3,563,004 A | 2/1971 | Schouw ........................ 55/103 |
| 3,777,457 A | 12/1973 | Laube .......................... 55/223 |
| 3,966,422 A | 6/1976 | Waters ......................... 55/316 |
| 4,043,776 A | 8/1977 | Orel ............................. 55/385 |
| 4,177,045 A | 12/1979 | Orel ............................. 55/102 |
| 4,488,888 A | 12/1984 | Doyle .......................... 55/481 |
| 4,905,340 A | 3/1990 | Gutschmit ............... 15/316 R |
| 5,085,134 A | * 2/1992 | Hofstra et al. ............... 454/67 |
| 5,141,539 A | * 8/1992 | Hiouani ..................... 55/385.1 |
| 5,325,876 A | * 7/1994 | Yang .......................... 131/242 |
| 5,400,541 A | 3/1995 | Ennamorato .................... 43/1 |
| 5,555,664 A | 9/1996 | Shockley .......................... 43/1 |
| 5,562,407 A | 10/1996 | Cielo ...................... 415/121.2 |

* cited by examiner

Primary Examiner—Jose' G. Dees
Assistant Examiner—Robert M. DeWitty

(57) ABSTRACT

A human scent control device including a collapsible conical housing having a bottom end of larger circumference than the top end and having a structural support means consisting of several rigid rings attached within said housing. An exhaust fan motor is affixed within the top of the housing for drawing human scent through one or more filters retained by the rings. The device is provided velcro straps to attach the device to a tree or stand to suspending the conical housing above the area occupied by a human.

8 Claims, 4 Drawing Sheets

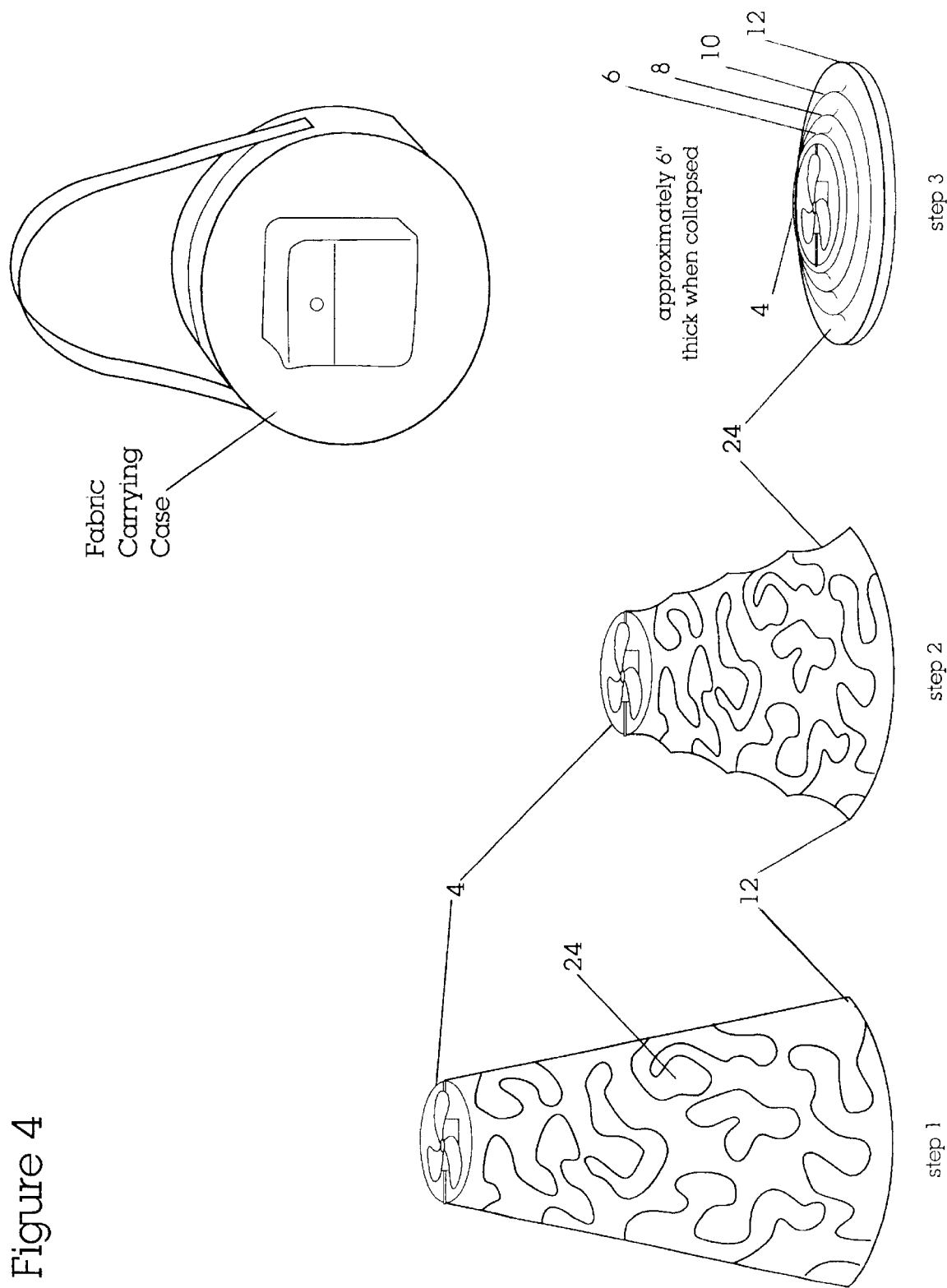

TOTAL SCENT CONTROL SYSTEM

FIELD OF THE INVENTION

The present invention relates to a portable human scent dissipating apparatus whose main purpose is to control, remove and dissipate all human and foreign scents within its circumference so that hunters, nature watchers, or photographers can conceal their scent from wild animals. More specifically, the present invention relates to a conically shaped housing having external camouflaged coloring and supported by circular metal rings which in turn contain scent masking or scent extracting filters. The apparatus mounts to a tree or stand and hangs above the hunter or photographer. The conical shape creates a chimney effect which, when coupled with an exhaust fan and heating coil, draws all human scent from beneath its housing upward through its "chimney" and eliminating or dissipating the odor-reduced human scent, or other foreign scents.

BACKGROUND OF THE INVENTION

Prior devices in the field of human scent control for hunters or nature watchers include scent masking clothing, animal scent imitation sprays, and similar devices which only serve to mask or cover up the human scent. None of these function to remove and dissipate the human scent.

Prior devices in the field of fan induced odor removal have been directed to absorbing odors from cigarettes and cigars, and other odor causing or contaminating articles. None of the devices are suitable for functioning as a portable human scent control or scent dissipating device. These devices typically require an electrical connection to an electric outlet of some kind. One such device which does not require an electrical connection and which is portable is known as "Hand-Held Odor Dissipating and Removing Device" U.S. Pat. No. 5,562,407 (Cielo). However, this device is too small to remove human scent and must be hand held. The present invention covers the circumferential area of the human body and mounts to a tree or stand, instead of being hand held. Also, Cielo is cylindrical, not conical, and does not incorporate a design to take advantage of the "chimney effect," as does the present invention.

SUMMARY OF THE INVENTION

An object of the present invention is to provide a portable collapsing conical "chimney" for outdoor use of hunters and nature watchers, which mounts above the human body and, with the use of support rings containing filters and a battery operated fan and/or a battery operated heating ring, captures and draws the human scent (and other scents) upwardly through the conical structure, reducing and masking the odor, and dissipating the reduced odor into the air above the human body.

Another object of the present invention is to provide a "hands free" camouflaged, portable, easy to carry total human scent control system, freeing both hands of a game hunter or nature photographer, and simultaneously removing and dissipating all human scent in accordance with the preceding object, thus allowing said hunter or photographer closer access to wild animals.

DESCRIPTION OF THE PREFERRED EMBODIMENT

The Total Human Scent Control System is comprised of a conically shaped housing general designated by reference 2, and metal support rings designated by references 4, 6, 8, 10 and 12. FIG. 1 is a side elevational view of the system, illustrating the relative locations of the support rings 4, 6, 8, 10 and 12, and of the heating element 22 and dissipating fan 20. The support rings 14, 16 and 18 have means to insert disposable filters for capturing or masking human scents. The preferred embodiment has scent capturing filters 16 and 18 in support rings 8 and 10, and a scent masking filter 14 in support ring 6, but the present invention is not limited to this configuration, or this quantity of support rings and filters.

The conical housing 2 is comprised of a collapsible material which has a camouflaged colored exterior to minimize visibility by wild animals. The device collapses about the support rings 4, 6, 8, 10 and 12, reducing the total thickness when not in use to about 3 inches, or less, as illustrated in FIG. 4.

The preferred embodiment shows the housing 2 as perfectly conical in shape, but the present invention is not limited to said conical shape. The present invention could have a collapsible housing which is, for example, pyramidal in shape, or could have a conical shape with a housing which curves outwardly toward the bottom support ring, or in other words, a conical housing with a diameter which increases algebraically rather than linearly toward the bottom support ring.

The preferred embodiment also consists of metal support arms designated by references 26 and 28, as illustrated on FIG. 4. These support arms 26 and 28 have means to attach to the upper support ring 4, and also have means to mount said scent control system to a tree or pole so as to position the system above the body of a hunter, photographer, or nature watcher.

BRIEF DESCRIPTION OF THE DRAWINGS

FIG. 4 is a perspective view. Illustrating how the system collapses into a nearly flat, easily portable device.

Figure 1:
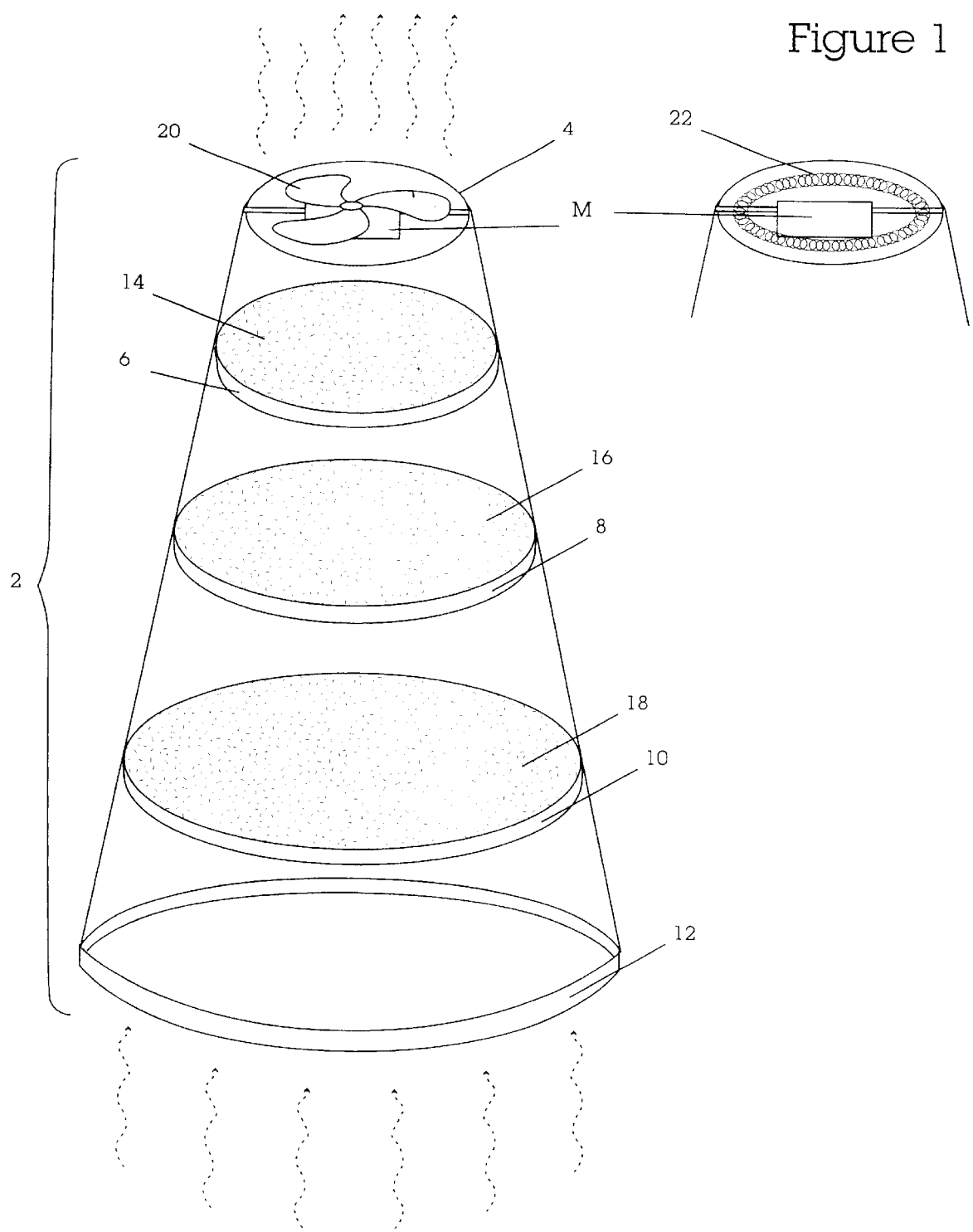
FIG. 1 is a side elevational view of the conically shaped system illustrating relative locations of the support rings with inserted filters, heating coil and fan.
Figure 2:
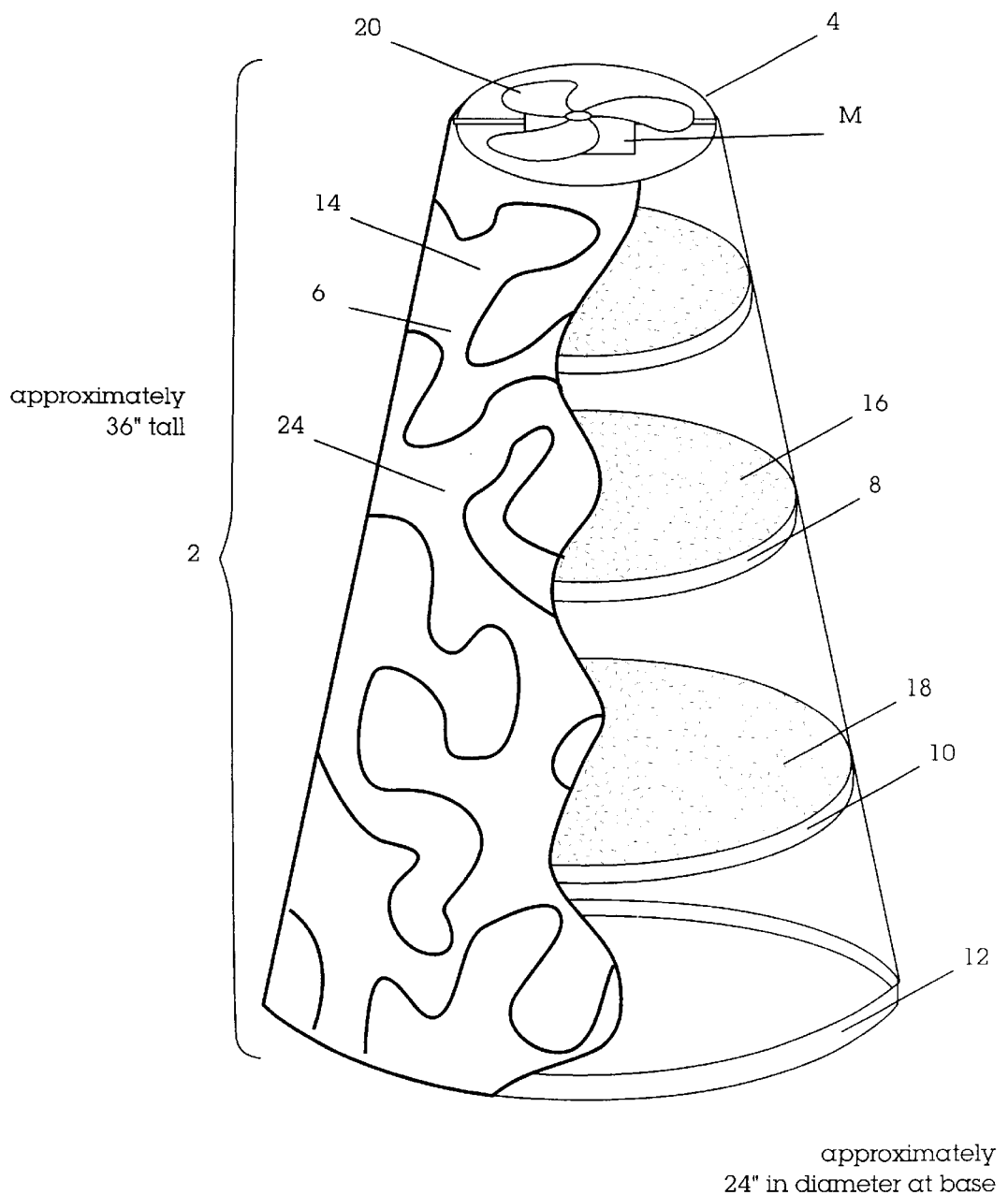
FIG. 2 is a sectional perspective view of the system also illustrating the camouflaged exterior.
Figure 3:
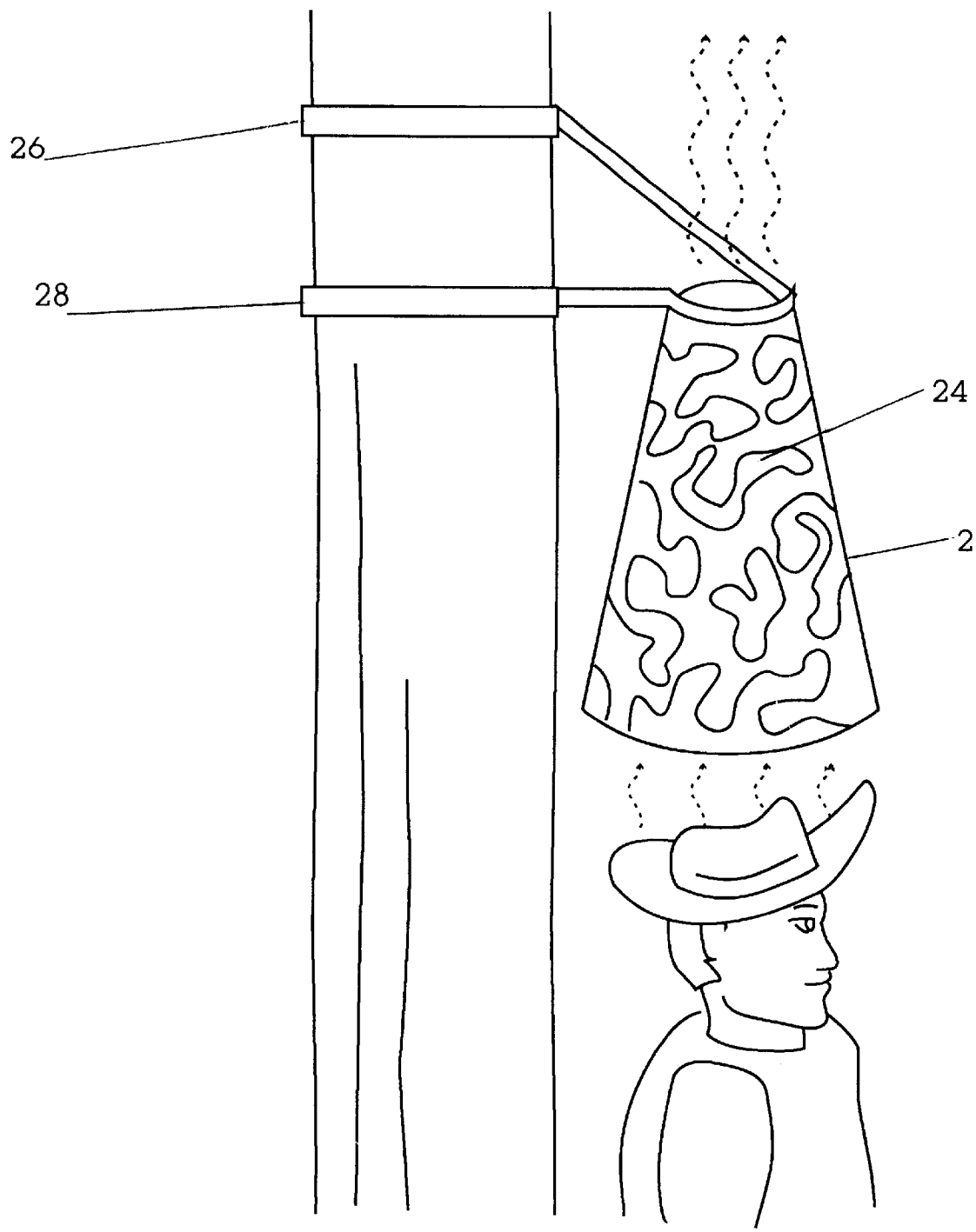
FIG. 3 is a side elevational view illustrating an exemplary method of mounting the device on a tree above a hunter or photographer.

| | |
|---|---|
| 2 | Conical Housing |
| 4, 6, 8, 10, 12 | Support Rings |
| 14 | Scent Masking Filter |
| 16, 18 | Scent Filters |
| 20 | Exhaust Fan |
| 22 | Heating Coil |
| 24 | Camouflaged Exterior |
| 26 | Support Arm |
| 28 | Support Arm |

I claim:

1. A portable collapsible human scent dissipating apparatus comprising a human scent control device comprising:

a conical housing having a top end and having a bottom end of larger circumference than the top end;

a collapsible structural support means comprising five rigid rings that are secured to the conical housing in several parallel spaced positions therein within said housing;

an exhaust fan motor affixed within said top end;

at least one filter containing a portable human scent masking material retained by said structural support means;

an attachment means for suspending said housing above a human.

2. A portable collapsible human scent dissipating apparatus comprising a human scent control device as claimed in claim 1 in which said structural support means includes:

a first ring attached to said top end and having said exhaust fan attached to the first ring;

a second ring attached below said first ring and having a first filter attached to the second ring.

3. A portable collapsible human scent dissipating apparatus comprising a human scent control device as claimed in claim 1 in which said structural support means includes:

a first ring attached to said top end and having said exhaust fan attached to the first ring;

a second ring attached below said first ring and having a first filter attached to the second ring;

a third ring attached below said second ring and having a second filter attached to the third ring.

4. A portable collapsible human scent dissipating apparatus comprising a human scent control device as claimed in claim 1 in which said structural support means includes:

a first ring attached to said top end and having said exhaust fan attached to the first ring;

a second ring attached below said first ring and having a first filter attached to the second ring;

a third ring attached below said second ring and having a second filter attached to the third ring;

a fourth ring attached below said third ring and having a third filter attached to the fourth ring.

5. A portable collapsible human scent dissipating apparatus comprising a human scent control device as claimed in claim 1 in which said structural support means includes:

a first ring attached to said top end and having said exhaust fan attached to the first ring;

a second ring attached below said first ring and having a first filter attached to the second ring;

a third ring attached below said second ring and having a second filter attached to the third ring;

a fourth ring attached below said third ring and having a third filter attached to the fourth ring.

a fifth ring attached to said bottom end below said fourth ring.

6. A portable collapsible human scent dissipating apparatus comprising a human scent control device as claimed in claim 1 in which said attachment means includes velcro straps attached to said structural support means.

7. A portable collapsible human scent dissipating apparatus comprising a human scent control device as claimed in claim 1 in which said rings are made of plastic.

8. A portable collapsible human scent dissipating apparatus comprising a human scent control device as claimed in claim 5 in which said first filter is a scent masking filter.

* * * * *